United States Patent [19]

Gerstenberger

[11] Patent Number: 5,043,852
[45] Date of Patent: Aug. 27, 1991

[54] APPARATUS ENABLING SELF-EXAMINATION OF THE PUBIC AREA

[76] Inventor: Roland W. Gerstenberger, P.O. Box 828, Arden, N.C. 28704

[21] Appl. No.: 483,754

[22] Filed: Feb. 23, 1990

[51] Int. Cl.⁵ ............................................. F21V 33/00
[52] U.S. Cl. ..................................... 362/129; 362/139
[58] Field of Search ............... 362/135, 136, 137, 138, 362/139, 140, 141, 142, 143, 144, 154, 155, 156, 128, 129; 128/3, 21, 22; 312/324, 224, 225

[56] References Cited

U.S. PATENT DOCUMENTS

| | | | |
|---|---|---|---|
| 1,692,943 | 11/1928 | Lelyveld | 128/22 |
| 1,743,469 | 1/1930 | May | 128/22 |
| 2,136,832 | 11/1958 | Weisberger | 128/22 |
| 2,683,453 | 7/1954 | Tong | 128/33 |
| 3,381,120 | 4/1968 | Fleisher et al. | 362/141 |
| 3,493,225 | 2/1970 | Ceraldi | 269/322 |
| 3,776,540 | 12/1973 | Comando | 269/328 |
| 3,814,414 | 6/1974 | Chapa | 269/323 |
| 3,989,359 | 11/1976 | Shirtt | 128/21 |
| 4,180,254 | 12/1979 | Lee et al. | 269/328 |
| 4,284,268 | 8/1981 | Gauthier | 269/328 |
| 4,623,955 | 11/1986 | Santini | 362/135 |
| 4,925,285 | 5/1990 | Dowdell et al. | 312/324 |

FOREIGN PATENT DOCUMENTS 478756  4/1953  Italy .

*Primary Examiner*—Ira S. Lazarus
*Assistant Examiner*—Sue Hagarman
*Attorney, Agent, or Firm*—David M. Carter

[57] ABSTRACT

There is provided a bench to facilitate the self-examination, shaving, and/or cleansing of the user's pubic area. The bench includes a cavity which is covered by an operable top. A light and a mirror are received in the cavity. The bench includes one or more foot supports. The mirror is mechanically linked to the top so that when the top is opened the mirror will move out of the cavity. The mirror is adjustable to permit the user to readily observe the pubic area.

9 Claims, 3 Drawing Sheets

APPARATUS ENABLING SELF-EXAMINATION OF THE PUBIC AREA

BACKGROUND OF THE INVENTION

This invention relates to means for examining the pubic area. More particularly relates to an apparatus to enable self-examination of the pubic area.

With the advent of women's bathing attire in the form of small bikinis and V-cut swimsuits, many women have found it desirable to shave in the pubic region so as to avoid exposure of pubic hairs. Because of the location of that region of the body, it is difficult for an individual to easily shave herself. One of the main problems is that much of the pubic region is not visibly accessible by self-examination.

In the past women have attempted to use hand mirrors to as assist in the shaving process, however this has proven to be awkward and not very effective.

OBJECTS OF THE INVENTION

It is therefore one object of this invention to provide an apparatus for enabling one to more readily have visual access to one's pubic area.

It is another object to provide an apparatus to enable one to more readily shave, inspect, and cleanse one's pubic area.

SUMMARY OF THE INVENTION

In accordance with one form of this invention there is provided an apparatus for enabling visual inspection of the pubic area by the user which includes a housing having a cavity therein. A mirror is received in the cavity. The housing includes a movable top for covering and uncovering the cavity. Upon the uncovering of the cavity, the user may visually observe the user's pubic region as reflected in the mirror.

Preferably a light is received in the cavity which is directed upwardly toward the user's pubic region. It is also preferred that the bench include at least foot support portion so that the user may place her foot thereon providing greater exposure of the pubic region. It is also preferred that the mirror be mechanically coupled to the top so that as the top is opened, the mirror will move out of the cavity toward the user's pubic region. The mirror should also be adjustable to accommodate the individual user. It is also preferred that the apparatus be in the form of a bench which when not being used as described above may be used as a piece of furniture.

BRIEF DESCRIPTION OF THE DRAWINGS

The subject matter which is regarded as the invention is set forth in the appended claims. The invention itself however may be better understood in reference to the accompanying drawings in which:

DESCRIPTION OF THE PREFERRED EMBODIMENT

Figure 1:
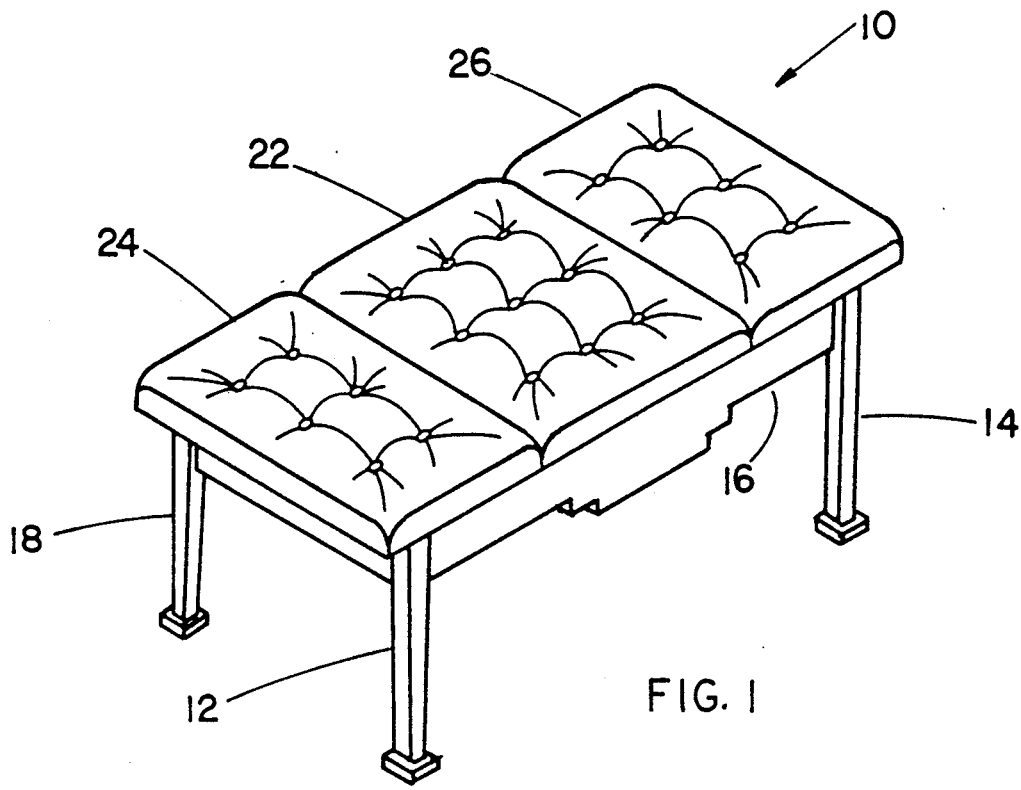
FIG. 1 is a plan view of the apparatus of the subject invention with the top closed.
Figure 3:
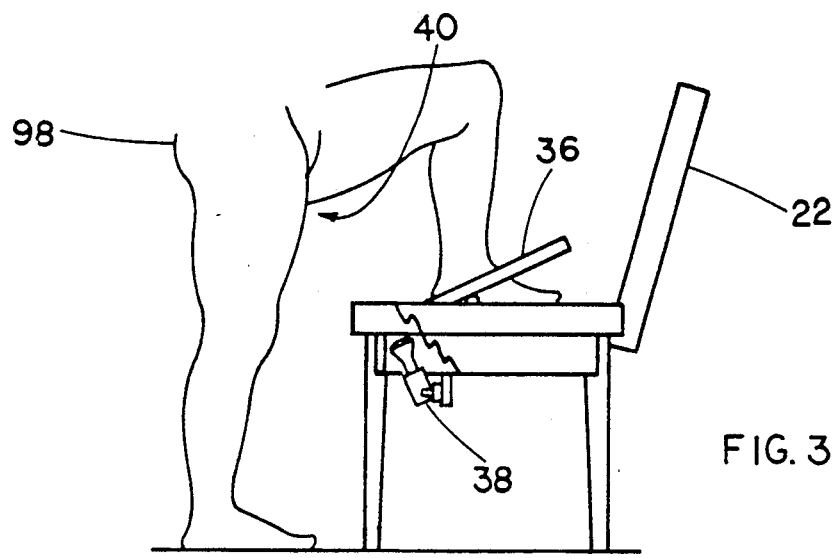
FIG. 3 is a side elevational view of the apparatus of FIG. 2 while in use.

Referring now more particularly to FIG. 1, there is provided apparatus 10 in the form of a padded bench, any portion of the top of which may be used to sit on. The bench includes four supporting legs 12, 14, 16 and 18. The top of the bench includes movable top 22 in the center of the bench and fixed outer top portions 24 and 26. The outer tops are specifically adapted to receive one of the user's feet as shown in FIG. 3 to facilitate examination of the pubic region. The legs 12, 14, 16 and 18 are preferably approximately 12 to 24 inches in height. Thus the height of the top portions 24 and 26 from the ground will be approximately 12 to 24 inches which results in a comfortable position for the user when her foot is placed thereon.

Figure 2:
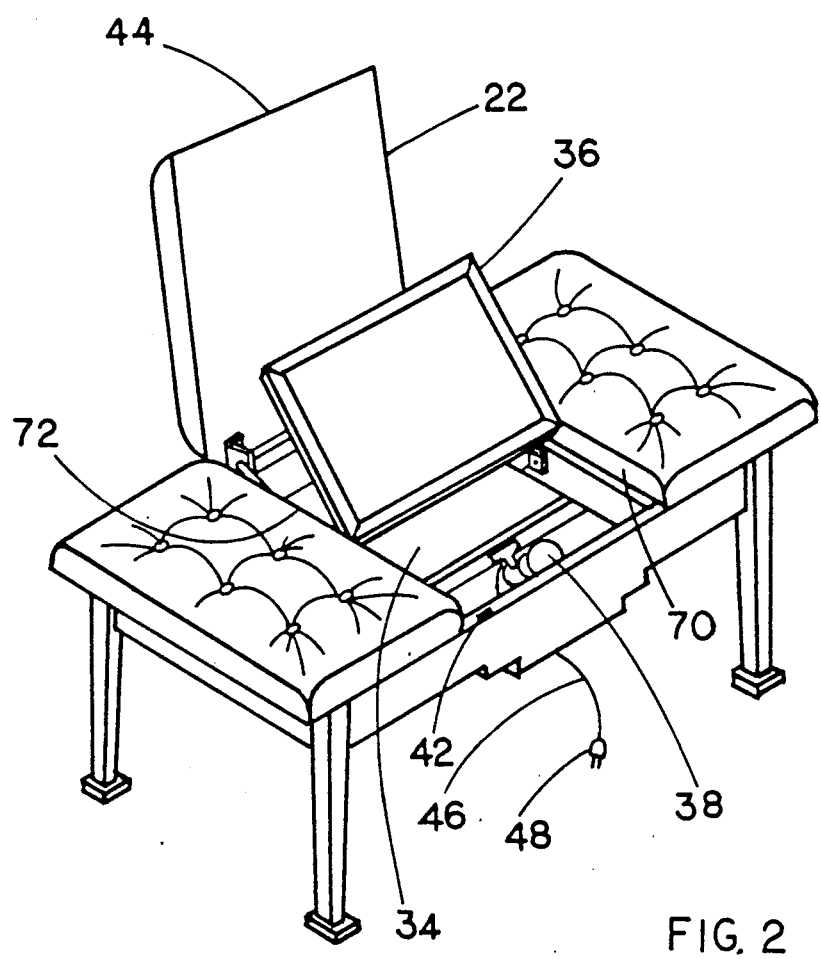
FIG. 2 is a plan view of the apparatus of FIG. 1 with the top open.

FIG. 2 shows hinged top 22 is in the open position. Top 22 is supported by hinges which permit the top to rotate. Opening top 22 exposes cavity 34. Cavity 34 primarily houses mirror 36 and its associated support structure and linkages, and electric lamp 38. Electric lamp 38, as shown in FIG. 3, points upwardly thereby illuminating pubic region 40 of the user as shown in FIG. 3. Electric lamp 38 is electrically connected to switch 42. Switch 42 is switched on and off by the action of top 22. When edge 44 of top 22 is in the down position it comes into contact with switch 42 and the switch is opened thereby turning off lamp 38. When top 22 is in the up position switch 42 is closed thereby turning on lamp 38. Switch 42 is connected to an electrical cord which is terminated by a plug (not shown).

Figure 4:
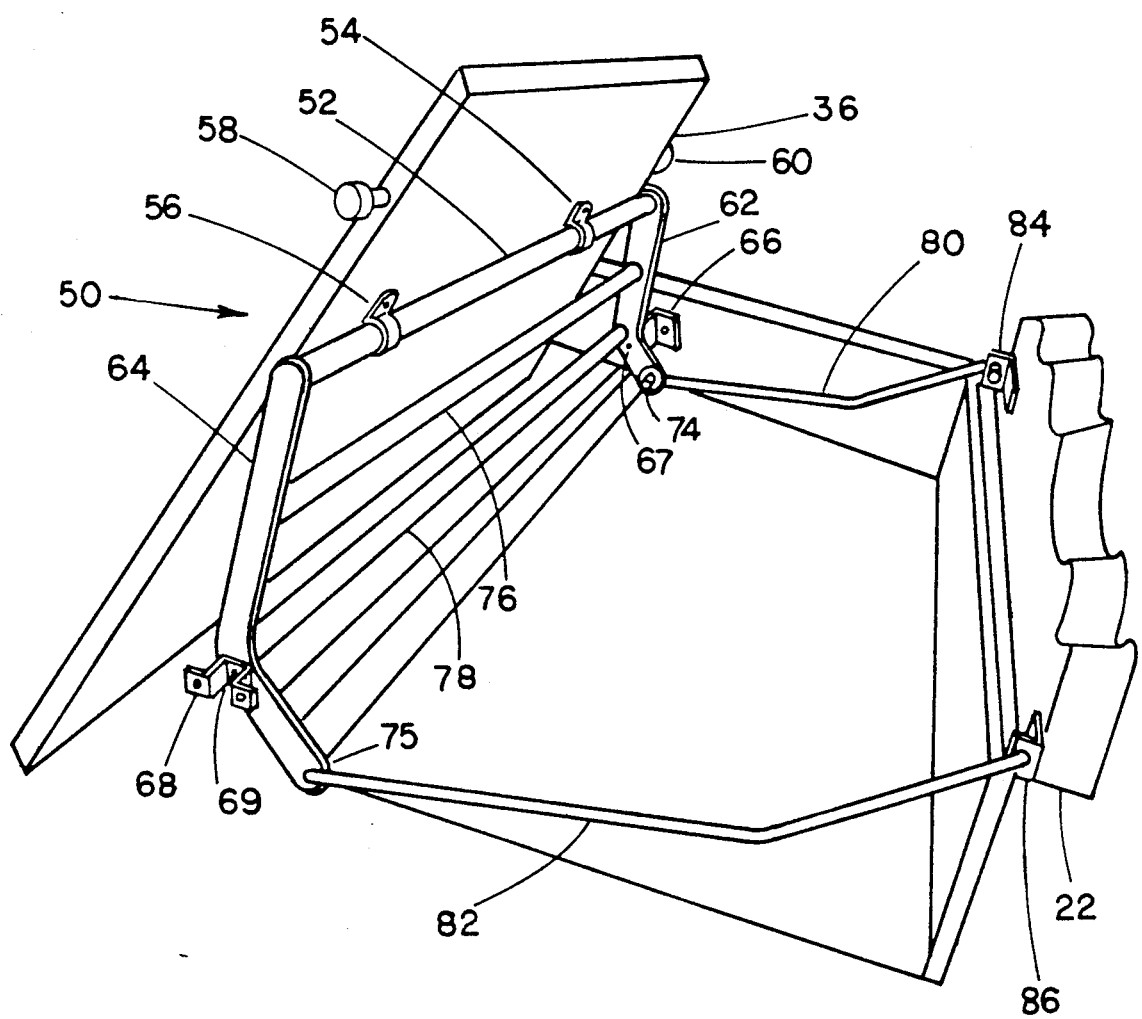
FIG. 4 is a plan view showing the details of the mechanical supports and linkages of the apparatus shown in FIG. 2.

FIG. 4 shows a more detailed version of the linkages and support structure for mirror 36. Mirror 36 is connected to support structure which is generally indicated as 50. Support structure 50 includes bar 52 which is rotatably attached to mirror 36 by brackets 54 and 56. Brackets 54 and 56 snugly hold mirror 36 to bar 52 but are loose enough to permit mirror 36 to be rotated about a portion of bar 52 by the use of handles 58 and 60. Thus the mirror is adjustable for a particular user. Bar 52 is connected to support rods 62 and 64 which are in turn rotatably connected to brackets 66 and 68 by pins 67 and 69, respectively. Brackets 66 and 68 are affixed to sides 70 and 72 of cavity 34. Bracket 62 is connected to pivot pin 74 of linkage 80. There is a corresponding pivot pin 75 of linkage 82 attached to rod 64. Stabilizing beams 76 and 78 are connected between rods 62 and 64 to add strength to the support structure. Linkage 80 connects rod 62 to bracket 84 which in turn is connected to top 22. Linkage 82 connects rod 64 to bracket 86 which in turn is also connected to top 22. Linkage 80 is permitted to move relative to rod 62 by its connection through pin 74, and linkage 82 is permitted to move with respect to rod 64 by its connection through pin 75. Thus the vertical movement of the mirror 36 in and out of cavity 34 is controlled by the opening and closing of top 22. This action may be better understood in reference to FIGS. 5 and 6.

Figure 5:
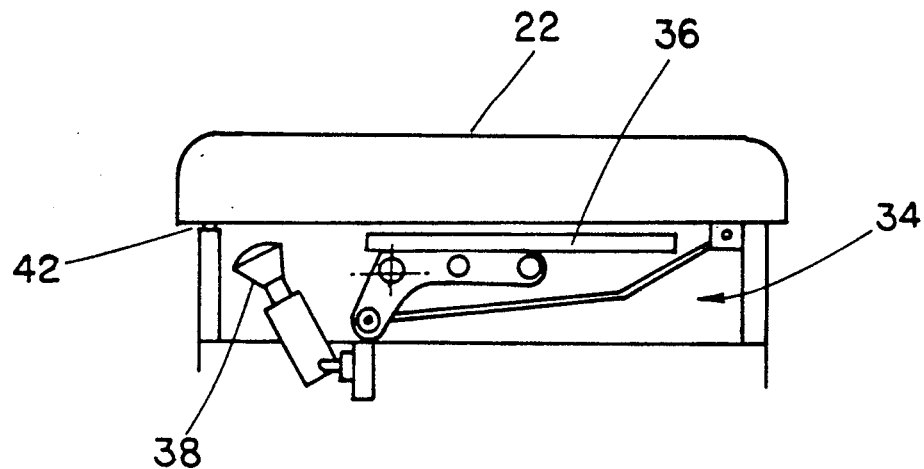
FIG. 5 is a partial side elevational view of the apparatus of FIG. 1 showing the linkages between the mirror and the top with the top in the down position.

FIG. 5 shows top 22 in its closed position and in contact with switch 42, thereby opening the circuit to lamp 38. With the top in the closed position, mirror 36 is in the down position within cavity 34 and thus hidden from view.

Figure 6:
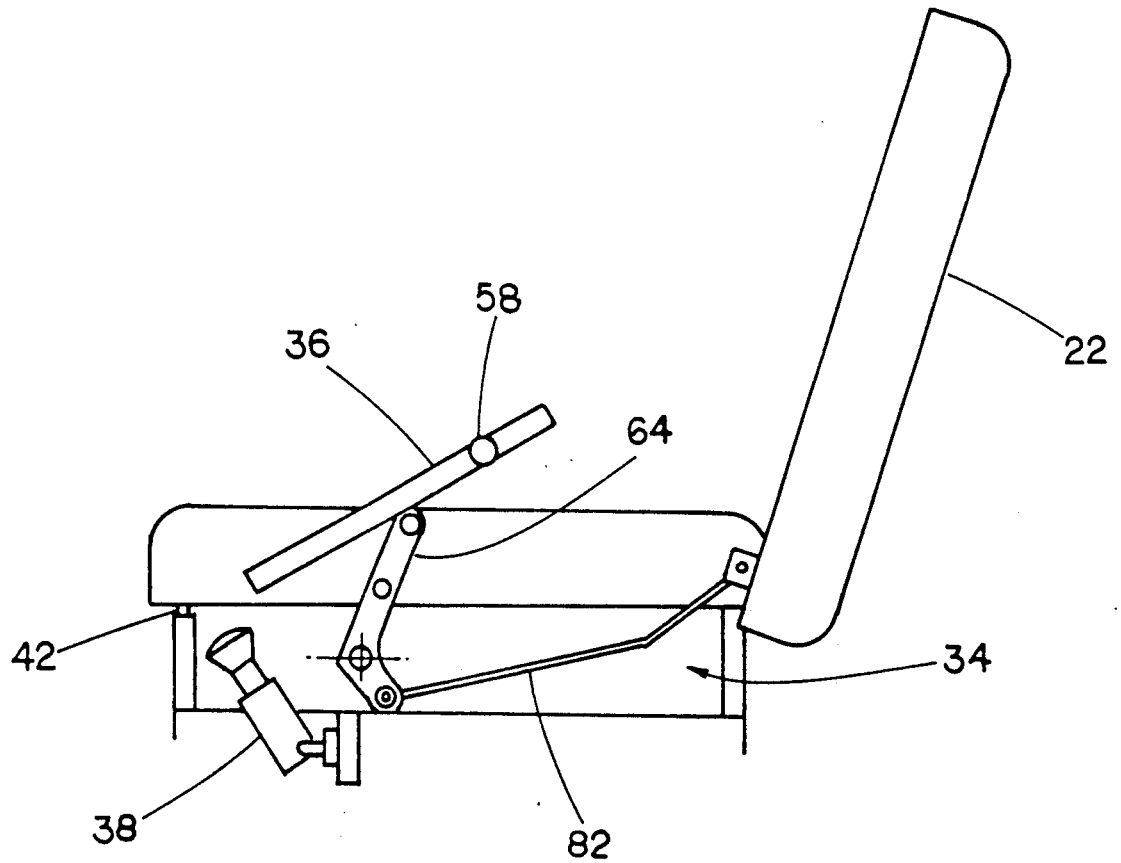
FIG. 6 is a side elevational view of the apparatus of FIG. 5, with the top in the up position.

As can be seen from FIG. 6 with top 22 in the open position, linkage 82 has been moved to the right thereby rotating rod 64 causing mirror 36 t rise out of cavity 34 to the position shown in FIG. 3 so that user 98 may readily view the pubic area 40. Switch 42 is closed thereby causing light 38 to come on, further enhancing the viewing of the pubic area. Thus an apparatus is provided to permit the user to self-examine the user's pubic area which also may be used as a seating bench.

From the foregoing description of the preferred embodiment of the invention, it will be apparent that many modifications may be made therein. It will be understood, however, that this embodiment of the invention is intended as an exemplification of the invention only and that the invention is not limited thereto. It should be understood therefore that it is intended in the appended claims to cover all such modifications as fall within the true spirit and scope of the invention.

I claim:

1. An apparatus for enabling visual inspection of the pubic area by the a comprising:
   a bench; said bench having a cavity therein;
   a mirror received in said cavity;
   said bench having a moveable top for covering and uncovering said cavity whereby upon the uncovering of said cavity the user may visually observe the user's pubic region as reflected in the mirror and whereby upon the covering of said cavity the user may use the top of the bench as a seat.

2. An apparatus as set forth in claim 1 further including a light source connected to said bench for enhancing the viewing of the pubic area.

3. An apparatus as set forth in claim 2 wherein said light source is located in said cavity and is directed upwardly.

4. An apparatus as set forth in claim 1 wherein said mirror is rotatable for alignment by the user.

5. An apparatus as set forth in claim 1 wherein said top is connected to said bench, said mirror mechanically coupled to said top; said mirror being enclosed in said cavity when said top is closed and said mirror being out of said cavity when said top is open.

6. An apparatus as set forth in claim 5 wherein said mirror is connected to a shaft for rotation thereabout.

7. An apparatus as set forth in claim 1 further including a platform on either side of said cavity whereby the user may place a foot on one of said platforms to enhance the viewing of the user's pubic area.

8. An apparatus as set forth in claim 1 wherein said mirror is mounted to a bracket assembly; said bracket assembly including mechanical linkages connecting to said top; said linkages enabling said bracket assembly to rotate thereby moving said mirror upwardly and downwardly upon the opening and closing of said top.

9. An apparatus as set forth in claim 8 further including means to rotate said mirror; said means to rotate including at least one handle connected to said mirror.

* * * * *